United States Patent
Chen et al.

(10) Patent No.: US 10,562,855 B2
(45) Date of Patent: *Feb. 18, 2020

(54) CRYSTALLINE FORM OF LENVANTINIB MESYLATE AND PROCESS OF PREPARATION THEREOF

(71) Applicant: CRYSTAL PHARMATECH CO., LTD., Suzhou, Jiangsu (CN)

(72) Inventors: Minhua Chen, Jiangsu (CN); Yanfeng Zhang, Jiangsu (CN); Xiaojuan Diao, Jiangsu (CN); Xiaoyu Zhang, Jiangsu (CN)

(73) Assignee: CRYSTAL PHARMATECH CO., LTD., Suzhou, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,114

(22) Filed: Mar. 25, 2019

(65) Prior Publication Data

US 2019/0218184 A1 Jul. 18, 2019

Related U.S. Application Data

(63) Continuation-in-part of application No. 15/575,352, filed as application No. PCT/CN2016/085360 on Jun. 8, 2016, now Pat. No. 10,246,418.

(51) Int. Cl.
C07D 215/48 (2006.01)
C07D 215/233 (2006.01)
A61P 35/00 (2006.01)

(52) U.S. Cl.
CPC .......... C07D 215/233 (2013.01); A61P 35/00 (2018.01); C07B 2200/13 (2013.01)

(58) Field of Classification Search
CPC .................................................. C07D 215/48
USPC .......................................... 546/153; 514/312
See application file for complete search history.

(56) References Cited

U.S. PATENT DOCUMENTS 6,627,646 B2 * 9/2003 Bakale .................. C07D 401/12
514/303
10,246,418 B2 * 4/2019 Chen ...................... A61K 31/47

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
Brittain ed., Polymorphism in Pharmaceutical Solids, Marcek Dekker, Inc., New York, pp. 235-238. (Year: 1999).*

* cited by examiner

*Primary Examiner* — Patricia L Morris
(74) *Attorney, Agent, or Firm* — VLP Law Group LLP; Kent H. Cheng (57) ABSTRACT

The present disclosure relates to a novel crystalline form of lenvatinib mesylate and the preparation method thereof. The novel crystalline form of mesylate of the present disclosure can be used for treating invasive and differentiated thyroid cancer. The novel crystalline form of mesylate of the present disclosure has good solubility, stability, and remarkable purification effect in process. The preparation method of this novel crystalline form is simple, low cost, and has an important value for future optimization and development of the drug.

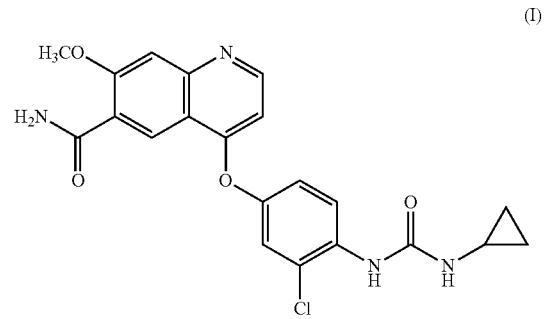

7 Claims, 8 Drawing Sheets

CRYSTALLINE FORM OF LENVANTINIB MESYLATE AND PROCESS OF PREPARATION THEREOF

RELATED APPLICATIONS

This application is a continuation-in-part of prior application Ser. No. 15/575,352 filed Nov. 18, 2017, which in turn is a U.S. national phase application of PCT/CN2016/085360, filed Jun. 8, 2016, the entire contents of which is incorporated by reference.

TECHNICAL FIELD

The present disclosure relates to the field of chemical pharmaceuticals, particularly relates to a novel crystalline form of lenvatinib mesylate and process of preparation and uses thereof.

BACKGROUND

Lenvatinib is an oral multiple receptor tyrosine kinase (RTK) inhibitors for treating invasive and differentiated thyroid cancer developed by Eisai Co., and was approved on Feb. 13, 2015 by FDA. Lenvatinib mesylate is used in the approved drug. The chemical name of the drug is 4-{3-Chloro-4-[(cyclopropylcarbamoyl) amino]phenoxy}-7-methoxy-6-quinolinecarboxamide, and the structure is shown as formula I:

(I)

Since different crystalline forms of the same compound are different in solubility and stability, absorption and bioavailability, and therapeutic effect will be affected. Thus, a comprehensive and systematic polymorph and salts screening to select the most suitable crystalline form or salt form for development cannot be ignored.

CN1890220A disclosed crystalline Form A, Form B, Form C, Form F and Form I of lenvatinib mesylate. Form α and Form β of lenvatinib ethanesulfonate was also disclosed. The inventors of the present disclosure surprisingly find novel crystalline Form M of lenvatinib mesylate. Form M is different from any form disclosed in CN1890220A. In addition, Form M of lenvatinib mesylate of the present disclosure has good stability and remarkable purification effect in process. The process of novel crystalline forms is simple, low cost, and has an important value for future optimization and development of the drug.

SUMMARY OF THE DISCLOSURE

One objective of the present disclosure is to provide a novel crystalline form of lenvatinib mesylate, designated as Form M, which can improve solubility of lenvatinib mesylate.

Lenvatinib mesylate is compound (I) mesylate (I)

The crystalline Form M of lenvatinib mesylate of the present disclosure, its X-ray powder diffraction pattern shows at least three characteristic peaks at 2theta values of 11.30±0.2°, 6.1°±0.2°, 15.2°±0.2°, 17.9°±0.2°, 23.5°±0.2°, 21.8°±0.2°, 7.9°±0.2°, 10.1°±0.2° and 22.8°+0.2°.

Preferably, one of said three characteristic peaks is at 2theta values of 11.3°±0.2°. More preferably, the other two of said three characteristic peaks are at 2theta values of 6.10°±0.2° and 15.2°±0.2°.

As a preferred example of the present disclosure: crystalline Form M of lenvatinib mesylate of the present disclosure, its X-ray powder diffraction pattern shows at least six characteristic peaks at 2theta values of 11.3°±0.2°, 6.1°±0.2°, 15.2°±0.2°, 17.9°±0.2°, 23.5°±0.2°, 21.8°±0.2°, 7.9°±0.2°, 10.1°±0.2° and 22.8°±0.2°. Preferably, three of the six characteristic peaks are at 2theta values of 11.3°±0.2°, 6.1°±0.2° and 15.2°±0.2°. More preferably, the other three of the six characteristic peaks are at 2theta values of 17.9°±0.2°, 23.5°±0.2° and 21.8°±0.2°.

According to a specific and preferred aspect of the present disclosure, the X-ray powder diffraction pattern of the crystalline Form M of lenvatinib mesylate shows characteristic peaks at 2theta values of 11.3°±0.2°, 6.1°±0.2°, 15.2°±0.2°, 17.9°±0.2°, 23.5°±0.2°, 21.8°±0.2°, 7.9°±0.2°, 10.10° 0.2° and 22.8°±0.2°.

Figure 1:
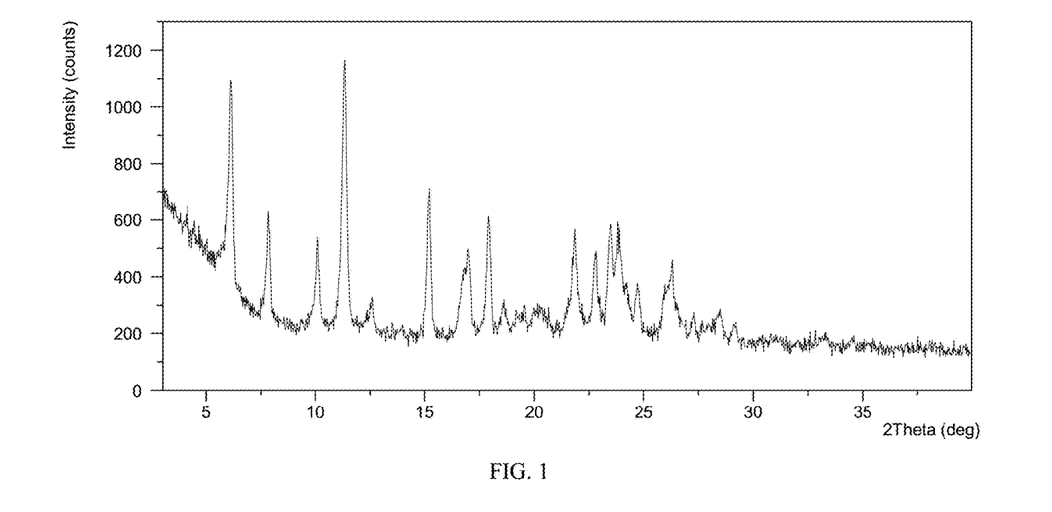
FIG. 1 shows an XRPD pattern of crystalline Form M of lenvatinib mesylate

According to a specific example, the X-ray powder diffraction pattern of the crystalline Form M of lenvatinib mesylate of the disclosure is substantially as shown in FIG. 1.

Figure 8:
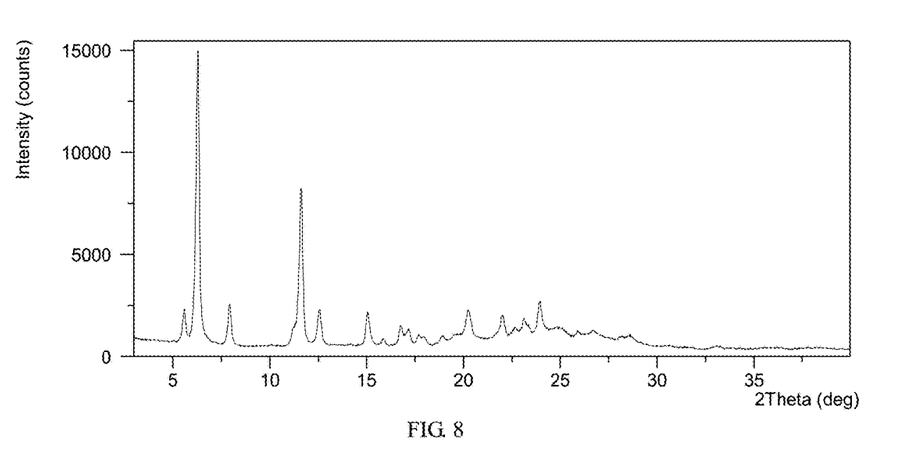
FIG. 8 shows an XRPD pattern of crystalline Form M of lenvatinib mesylate

According to a specific example, the X-ray powder diffraction pattern of the crystalline Form M of lenvatinib mesylate of the present disclosure is substantially as shown in FIG. 8.

Figure 2:
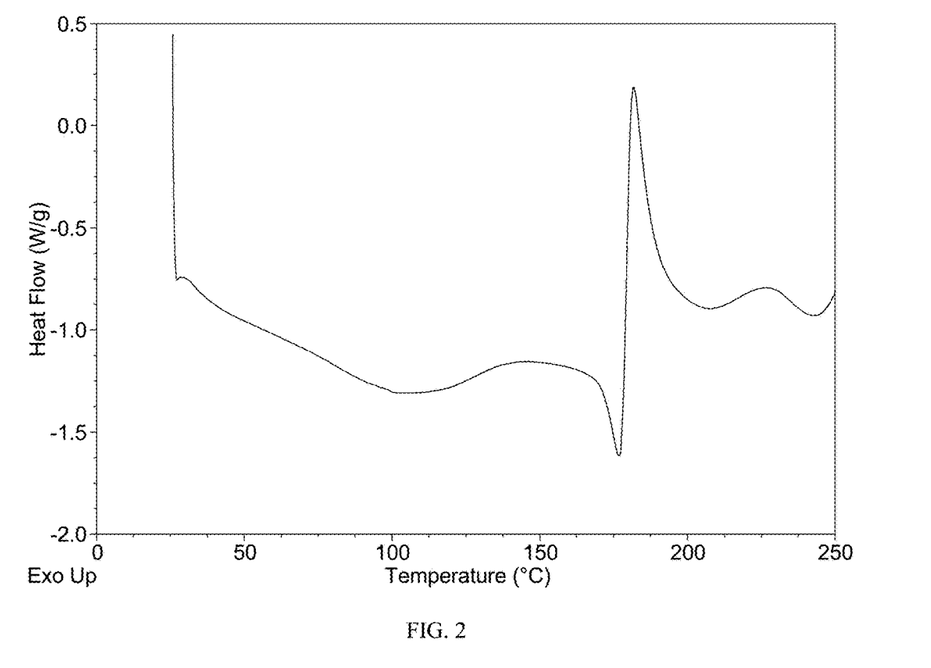
FIG. 2 shows a DSC thermogram of crystalline Form M of lenvatinib mesylate

According to a specific example, the differential scanning calorimetry analysis thermogram (DSC) of the crystalline Form M of lenvatinib mesylate of the disclosure is substantially as shown in FIG. 2.

Figure 3:
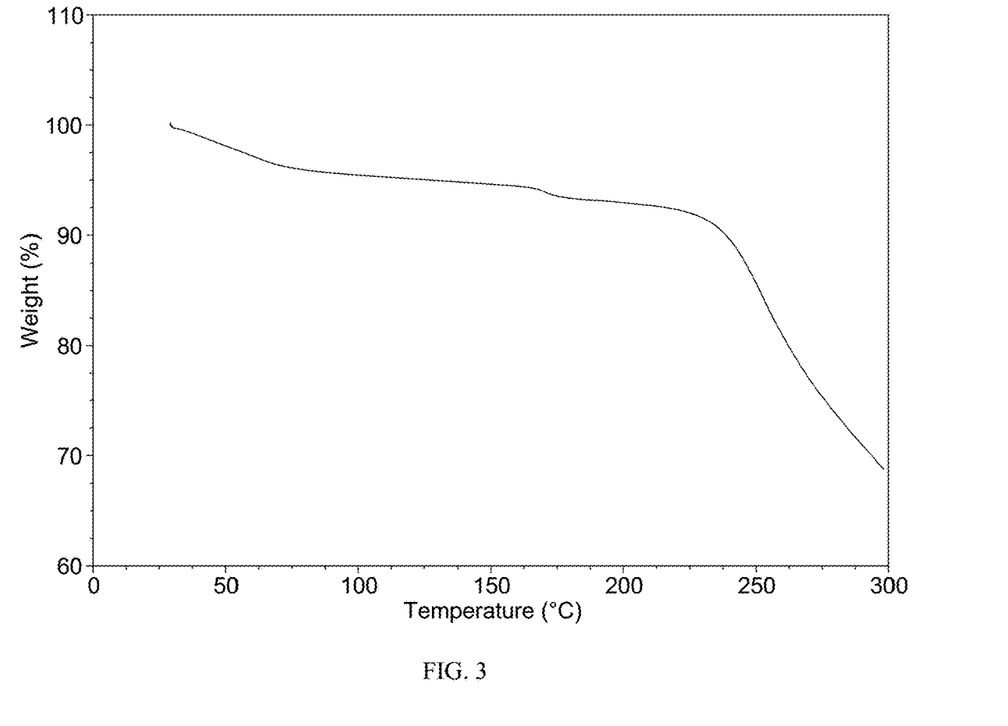
FIG. 3 shows a TGA thermogram of crystalline Form M of lenvatinib mesylate

According to a specific example, the thermal gravimetric analysis (TGA) thermogram of crystalline Form M of lenvatinib mesylate of the disclosure is substantially as shown in FIG. 3.

Another objective of the present disclosure is to provide a process for preparing crystalline Form M of lenvatinib mesylate, comprising adding compound (I) and methanesulfonic acid into an appropriate crystallizing solvent, stirring to get Form M.

Furthermore, the appropriate crystallizing solvent comprises single or mixed solvents selected from water, alcohols, ketones, nitriles, cyclic ethers, and aliphatic hydrocarbons.

Furthermore, the appropriate crystallizing solvents are nitriles or solvents containing nitriles, specifically, the crystallizing solvent is acetonitrile.

According to a specific aspect of the present disclosure, the process of crystalline Form M of lenvatinib mesylate comprises: adding lenvatinib powder in acetonitrile to obtain a suspension, and adding methanesulfonic acid dropwise into the suspension, then stirring at room temperature and centrifuging to give a solid, drying the solid overnight to get Form M. Furthermore, the stirring time is preferably over 12 hours, and more preferably is over 20 hours. The drying condition is preferably at room temperature.

Furthermore, the present disclosure provides another method for preparing crystalline Form M of lenvatinib mesylate, which has high yield and low solvent residue.

The preparation method comprises: suspending Form B of Lenvatinib in acetonitrile, adding acetonitrile solution of methanesulfonic acid slowly, then aging, vacuum filtering the resulting suspension under nitrogen protection to obtain a wet cake, drying the wet cake under vacuum to obtain Form M.

Further, said vacuum drying is followed by humid nitrogen purging.

Further, the said stirring and aging temperature is −10° C.-0° C., preferably −5° C.

The said concentration of acetonitrile solution of methanesulfonic acid is 25 μL/mL-250 μL/mL, preferably 64 μL/mL.

The said adding time of acetonitrile solution of methanesulfonic acid is preferably over 4 hours.

The said aging time is 3 hours-72 hours, preferably 5 hours.

The said humidity of humid nitrogen purging is 5% RH-35% RH, preferably 20% RH-30% RH.

The said nitrogen purging is for 24 hours.

Form B of Lenvatinib used here was disclosed in US20070117842A1 which has characteristic peaks at 2theta values of 21.75°±0.2°, 12.430±0.2° and 16.56±0.2°. Another objective of the present disclosure is to provide a pharmaceutical composition comprising an effective dose of crystalline Form M of lenvatinib mesylate and pharmaceutical acceptable excipients.

Furthermore, the crystalline Form M of lenvatinib mesylate of the pharmaceutical composition of the present disclosure can be used for preparing drugs treating cancers, especially preparing pharmaceutical formulations treating thyroid cancer.

Said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, oven or vacuum oven.

The present disclosure provides crystalline Form M of lenvatinib mesylate for preparing a drug for treating cancers, especially for the use of preparing drugs treating thyroid cancer.

The present disclosure has the following advantages:

Comparing with crystalline forms of lenvatinib mesylate in prior art, the crystalline Form M of lenvatinib mesylate has improved solubility. In addition, the crystalline Form M of lenvatinib mesylate of the present disclosure has good stability (Crystal transformation during drug storage and development can be avoided, so the change of bioavailability and efficacy can be avoided), good crystal morphology, and remarkable purification effect in process. The preparation method of novel crystalline forms is simple, low cost, and has an important value for future optimization and development of the drug.

DETAILED DESCRIPTION

The present disclosure will be further explained by the specific examples, but the disclosure is not intended to limit the scope of the present disclosure. The skilled in the art can make improvements to the process of preparation and the used instruments within the scope of the claims, and those improvements should be considered as falling into the scope of the present disclosure. Therefore, the scope of the present disclosure patent should be defined by the claims.

In the following examples, the experimental methods were implemented generally in accordance with conventional conditions or conditions recommended by the manufacturers.

The abbreviations used in the disclosure are explained as follows:

XRPD: X-ray Powder Diffraction
DSC: Differential Scanning Calorimetry
TGA: Thermal Gravimetric Analysis
$^1$H NMR: $^1$H Nuclear Magnetic Resonance
PSD: Particle Size Distribution X-ray powder diffraction pattern of the present disclosure is collected by a Panalytical Empyrean X-ray powder diffractometer. The parameters of the X-ray powder diffraction method of the present disclosure are as follows:

X-ray Reflection: Cu, Kα
Kα1 (Å): 1.540598; Kα2 (Å): 1.544426
Kα2/Kα1 intensity ratio: 0.50

Voltage: 45 (kV)
Current: 40 (mA)
Scan range: from 3.0 degree to 40.0 degree
Differential scanning calorimetry (DSC) data in the present disclosure is collected by a TA Q2000. The parameters of the differential scanning calorimetry (DSC) method of the present disclosure are as follow:
Heating rate: 10° C./min
Purge gas: nitrogen.
Thermal gravimetric analysis (TGA) data in the present disclosure is collected by a TA Q5000. The parameters of the thermal gravimetric analysis (TGA) method of the present disclosure were as follow:
Heating rate: 10° C./min;
Purge gas: nitrogen.
The particle size distribution data in the present disclosure tere acquired by an S3500 laser particle size analyzer of Microtrac. Microtrac S3500 is equipped with the SDC (Sample Delivery Controller). The test was carried out in wet mode, and the dispersion medium is Isopar G. The parameters are as follows:

| | |
| --- | --- |
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Polarized light microscopy (PLM): Polarized light microscopy image is collected by an Axio Lab. A1 upright microscope at room temperature.

Example 1

Process for Preparing Crystalline Form M of Lenvatinib Mesylate:

50.2 mg of lenvatinib was added into 4.0 mL of acetonitrile to obtain a suspension, and 10 μL of methanesulfonic acid (mass concentration: 99.5%) was dropwise added to the suspension, then it was stirred at room temperature for 24 hours and centrifuged to obtain solid. The solid was dried at 25° C. overnight, and the obtained solid was identified as crystalline Form M of lenvatinib mesylate.

Figure 4:
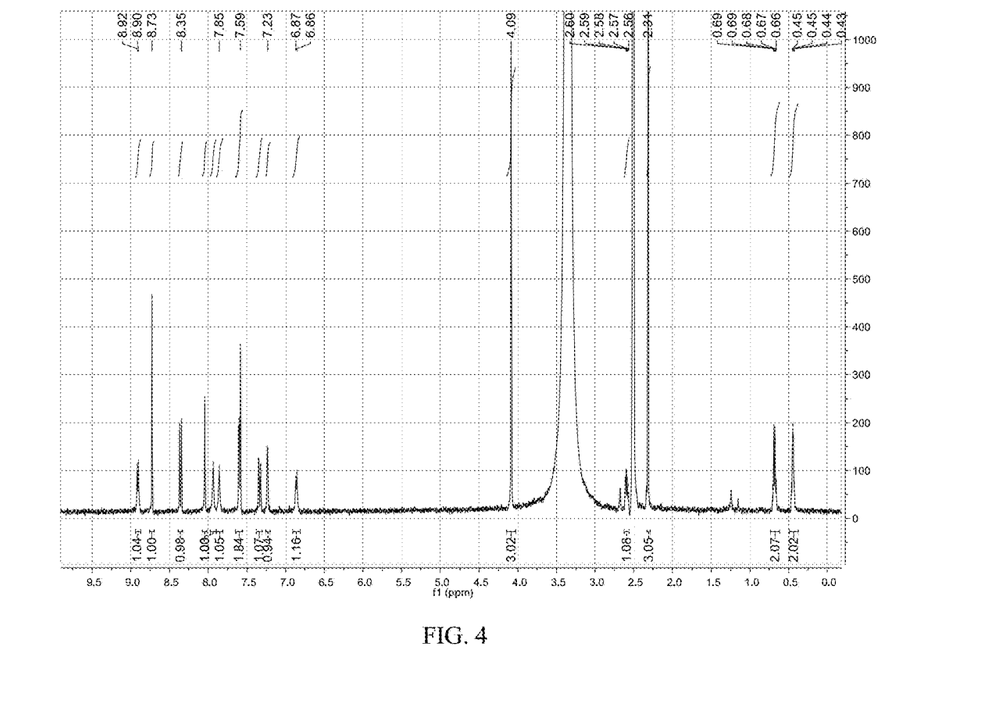
FIG. 4 shows a $^1$HNMR spectrum of crystalline Form M of lenvatinib mesylate
Figure 5:
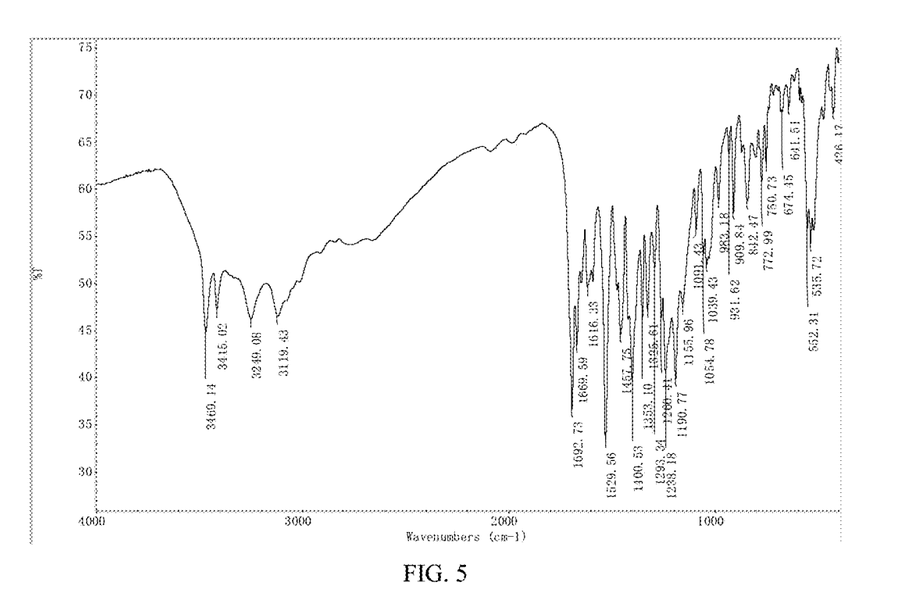
FIG. 5 shows an Infrared spectrum of crystalline Form M of lenvatinib mesylate

The XRPD pattern of Form M of the example is displayed in FIG. 1, the $^1$H NMR spectrum is displayed in FIG. 4. The IR spectrum is displayed in FIG. 5. Among them:
The XRPD data is listed in Table 1.

TABLE 1

| 2 theta (°) | d spacing | Intensity % |
| --- | --- | --- |
| 6.14 | 14.40 | 75.59 |
| 7.85 | 11.26 | 33.94 |
| 10.07 | 8.78 | 33.61 |
| 11.34 | 7.81 | 100.00 |
| 12.55 | 7.05 | 11.76 |
| 15.19 | 5.83 | 53.50 |
| 16.99 | 5.22 | 32.29 |
| 17.90 | 4.96 | 45.13 |

TABLE 1-continued

| 2 theta (°) | d spacing | Intensity % |
| --- | --- | --- |
| 18.54 | 4.78 | 12.19 |
| 19.38 | 4.58 | 7.49 |
| 20.13 | 4.41 | 10.55 |
| 21.83 | 4.07 | 41.20 |
| 22.80 | 3.90 | 32.45 |
| 23.46 | 3.79 | 43.92 |
| 23.80 | 3.74 | 43.36 |
| 24.72 | 3.60 | 20.03 |
| 26.28 | 3.39 | 30.01 |
| 27.26 | 3.27 | 10.06 |
| 28.50 | 3.13 | 11.88 |
| 29.15 | 3.06 | 7.19 |
| 30.99 | 2.89 | 2.58 |
| 33.25 | 2.69 | 3.62 |

$^1$H NMR data is shown in the following:
$^1$H-NMR (400 MHz, DMSO-d$_6$) δ 8.91 (d, J=6.0 Hz, 1H), 8.73 (s, 1H), 8.36 (d, J=9.1 Hz, 1H), 8.04 (s, 1H), 7.93 (s, 1H), 7.85 (s, 1H), 7.56-7.64 (m, 2H), 7.34 (dd, J1=9.1 Hz, J2=2.7 Hz, 1H), 7.24 (d, J=2.9 Hz, 1H), 6.86 (d, J=5.4 Hz, 1H), 4.09 (s, 3H), 2.56-2.63 (m, 1H), 2.31 (s, 3H), 0.65-0.72 (m, 2H), 0.41-0.47 (m, 2H).

IR data is shown as follows:
Absorption peaks (cm$^{-1}$): 426.17, 535.72, 552.31, 641.51, 674.45, 750.73, 772.99, 842.47, 909.84, 931.62, 983.18, 1039.43, 1054.78, 1091.43, 1155.96, 1190.77, 1238.18, 1260.41, 1293.34, 1325.61, 1353.10, 1400.53, 1457.75, 1529.56, 1616.33, 1669.59, 1692.73, 3119.43, 3249.08, 3415.02, 3469.14.

Figure 6:
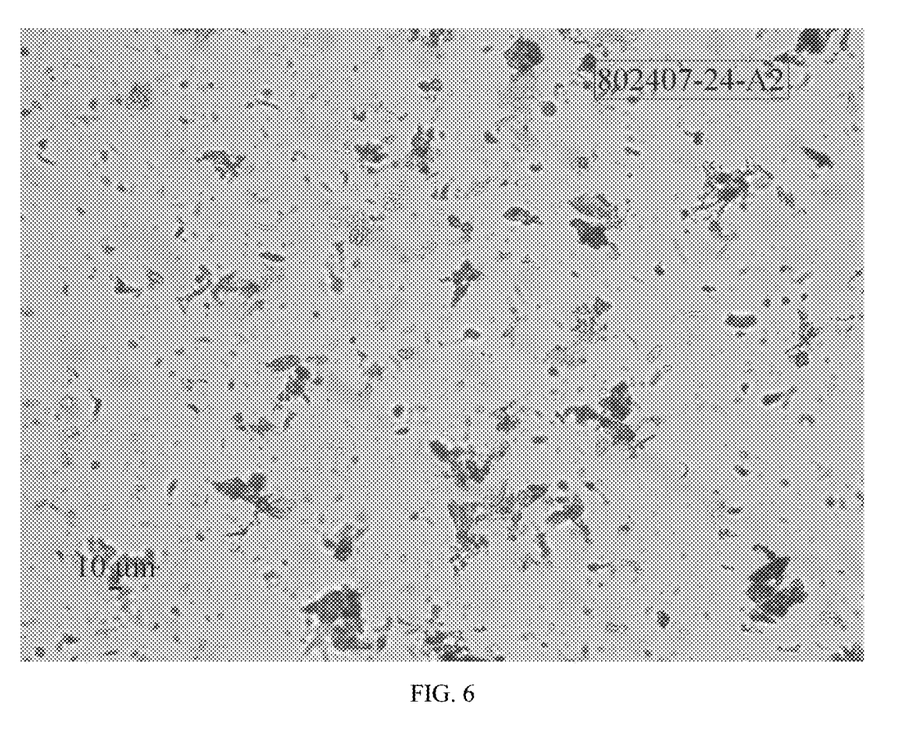
FIG. 6 shows a polarized light microscopy image of crystalline Form M of lenvatinib mesylate

The DSC thermogram of Form M is displayed in FIG. 2, the TGA thermogram is displayed in FIG. 3. The PLM image of Form M is displayed in FIG. 6, indicating the crystalline Form M has good crystal morphology and uniform particle size distribution.

Example 2

Process for Preparing Crystalline Form M of Lenvatinib Mesylate:

105.3 mg of lenvatinib powder was added into 12.0 mL of acetonitrile to obtain a suspension, and 30 μL of methanesulfonic acid (mass concentration: 99.5%) was dropwise added to the suspension, then it was stirred at room temperature for 24 hours and centrifuged to obtain solid. The solid was dried at 25° C. overnight, and the obtained solid was identified as crystalline Form M of lenvatinib mesylate.

The X-ray powder diffraction data of Form M of the example is listed in Table 2.

TABLE 2

| 2 theta (°) | d spacing | Intensity % |
| --- | --- | --- |
| 6.12 | 14.45 | 76.19 |
| 7.77 | 11.38 | 28.62 |
| 10.07 | 8.78 | 21.83 |
| 11.34 | 7.81 | 100.00 |
| 12.56 | 7.05 | 8.67 |
| 15.18 | 5.84 | 46.69 |
| 17.00 | 5.22 | 28.50 |
| 17.91 | 4.95 | 47.27 |
| 18.61 | 4.77 | 17.60 |
| 20.17 | 4.40 | 14.60 |
| 21.78 | 4.08 | 50.93 |
| 22.71 | 3.92 | 36.31 |
| 23.44 | 3.80 | 54.89 |
| 23.83 | 3.73 | 50.46 |
| 24.74 | 3.60 | 27.04 |

TABLE 2-continued

| 2 theta (°) | d spacing | Intensity % |
|---|---|---|
| 26.30 | 3.39 | 37.22 |
| 28.46 | 3.14 | 17.39 |
| 33.09 | 2.71 | 5.53 |
| 35.65 | 2.52 | 2.98 |

Example 3

Solubility Comparison Between Crystalline Form M of Lenvatinib Mesylate of the Present Disclosure and Anhydrate Form C in Patent CN1890220A:

Crystalline Form M of lenvatinib mesylate prepared in example 1 and anhydrate Form C in CN1890220A were prepared into saturated solution in pH 1.8 SGF (Simulated gastric fluid), pH 5.0 FeSSIF (Fed state simulated intestinal fluid), FaSSIF (Fasted state simulated intestinal fluid) and high purity water. Concentrations in the saturated solutions were determined after 24 hours by HPLC. The result is displayed in Table 3

TABLE 3

| Time point (h) | SGF | | FaSSIF | | FeSSIF | | High purity water | |
|---|---|---|---|---|---|---|---|---|
| | Form C | Form M | Form C | Form M | Form C | Form M | Form C | Form M |
| Solubility (mg/mL) 24 | 0.64 | 0.69 | 0.0015 | 0.024 | 0.0003 | 0.0004 | 1.0 | 1.6 |

The result suggests that crystalline Form M of lenvatinib mesylate of the present disclosure has higher solubility in comparison with Form C in patent CN1890220A. Specially, Form M has evident advantage in solubility in FaSSIF and high purity water in comparison with Form C.

Example 4

Figure 7A:
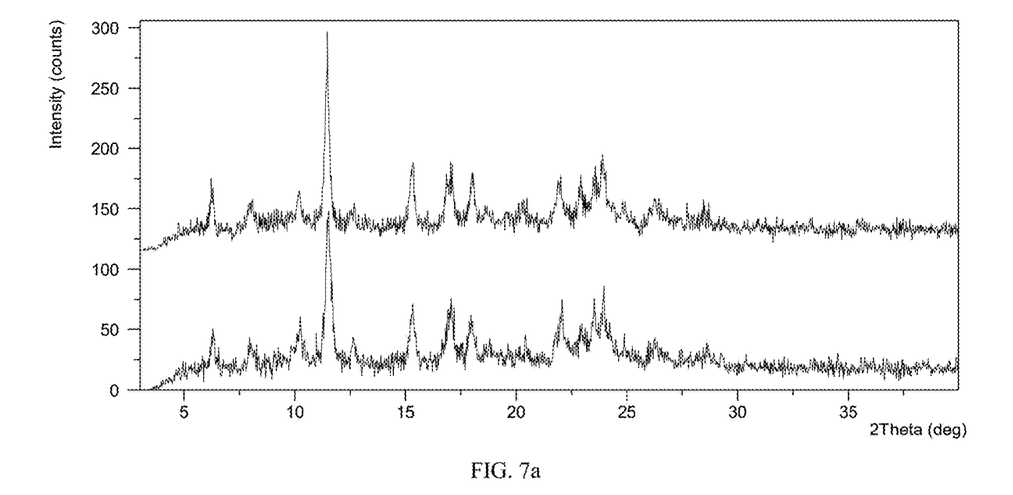
FIG. 7a~7c show XRPD patterns overlay of crystalline Form M of lenvatinib mesylate before and after stored in the following conditions for 7 days: a) sealed in aluminum plastic bags at 25° C./60% RH; b) sealed in aluminum plastic bags at 40° C./75% RH; c) sealed in aluminum plastic bags at 60° C./75% RH
Figure 7B:
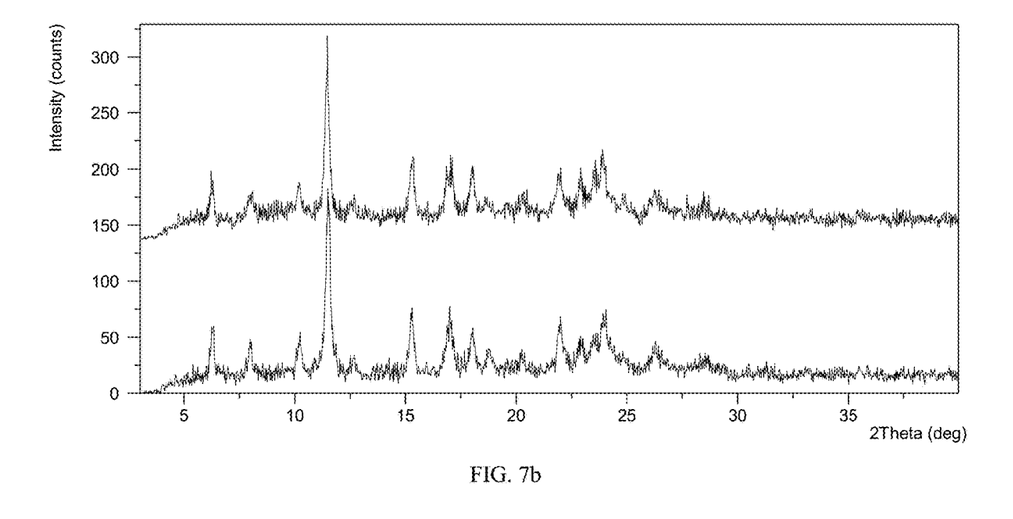
Figure 7C:
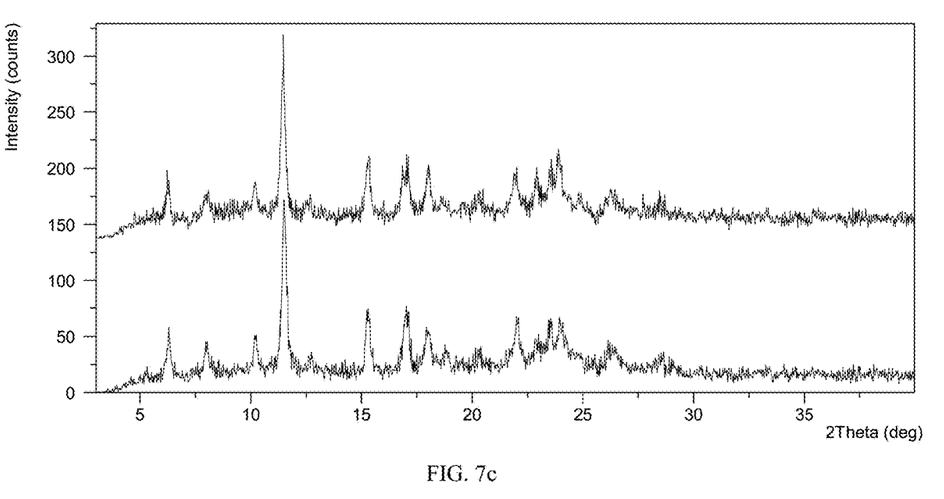

Stability Assessment of Form M of Lenvatinib Mesylate of the Present Disclosure:

Three samples of crystalline Form M of lenvatinib mesylate were stored under the following conditions: a) sealed in aluminum plastic bags at 25° C./60% RH; b) sealed in aluminum plastic bags at 40° C./75% RH; c) sealed in aluminum plastic bags at 60° C./75% RH. The samples were tested by XRPD before and after stored for 7 days. The XRPD patterns before and after storage are compared, and the results are displayed in FIG. 7a-7c. As shown in FIG. 7a-7c, Form M of the disclosure remained unchanged before and after storage, and the characteristic peaks maintain highly consistent. Thus indicates that the crystalline Form M of lenvatinib mesylate has excellent stability.

Example 5

10.03 g of Form B of Lenvatinib was added into 340 mL of acetonitrile and stirred at −5° C. with a speed of 200 r/min in 10 minutes. Then acetonitrile solution of methanesulfonic acid (the volumes of methanesulfonic acid and acetonitrile are 1.6 mL and 25 mL) was added in over 4 hours. Then the mixture was aged for 5 hours at −5° C. with a stirring speed of 150 r/min. Then the suspension was vacuum filtered under nitrogen protection for 10 minutes, and the obtained wet cake was vacuum dried to obtain a dry solid. The dry solid was purged under humid nitrogen (20% RH-30% RH) atmosphere for 24 hours to obtain the final product.

The obtained final product is Form M and the XRPD pattern of Form M of is displayed in FIG. 8 and the data are listed in Table 4.

TABLE 4

| 2θ | d spacing | Intensity % |
|---|---|---|
| 5.60 | 15.63 | 8.64 |
| 6.28 | 13.96 | 100.00 |
| 7.91 | 11.09 | 17.13 |
| 11.58 | 7.60 | 63.56 |
| 12.56 | 7.01 | 15.48 |
| 15.01 | 5.88 | 11.41 |
| 15.89 | 5.56 | 3.05 |
| 16.71 | 5.29 | 6.92 |
| 17.15 | 5.15 | 8.21 |
| 17.70 | 4.99 | 4.61 |
| 18.88 | 4.69 | 4.95 |
| 19.53 | 4.53 | 5.33 |
| 20.18 | 4.39 | 12.46 |
| 21.98 | 4.03 | 10.83 |
| 23.11 | 3.84 | 9.17 |
| 23.90 | 3.72 | 16.39 |

TABLE 4-continued

| 2θ | d spacing | Intensity % |
|---|---|---|
| 26.68 | 3.33 | 6.25 |
| 28.66 | 3.11 | 4.13 |

Figure 9:
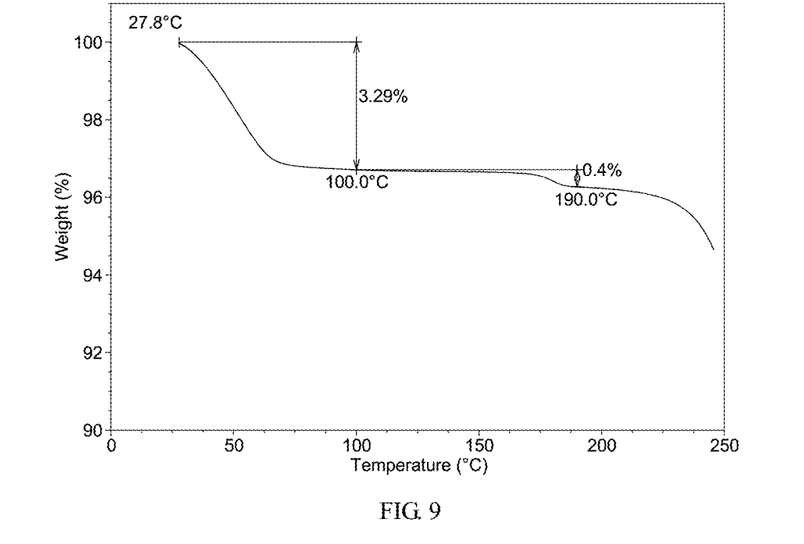
FIG. 9 shows a TGA thermogram of crystalline Form M of lenvatinib mesylate

The TGA thermogram of Form M shows about 3.3% weight loss when heated to 100° C., which is depicted in FIG. 9.

Figure 10:
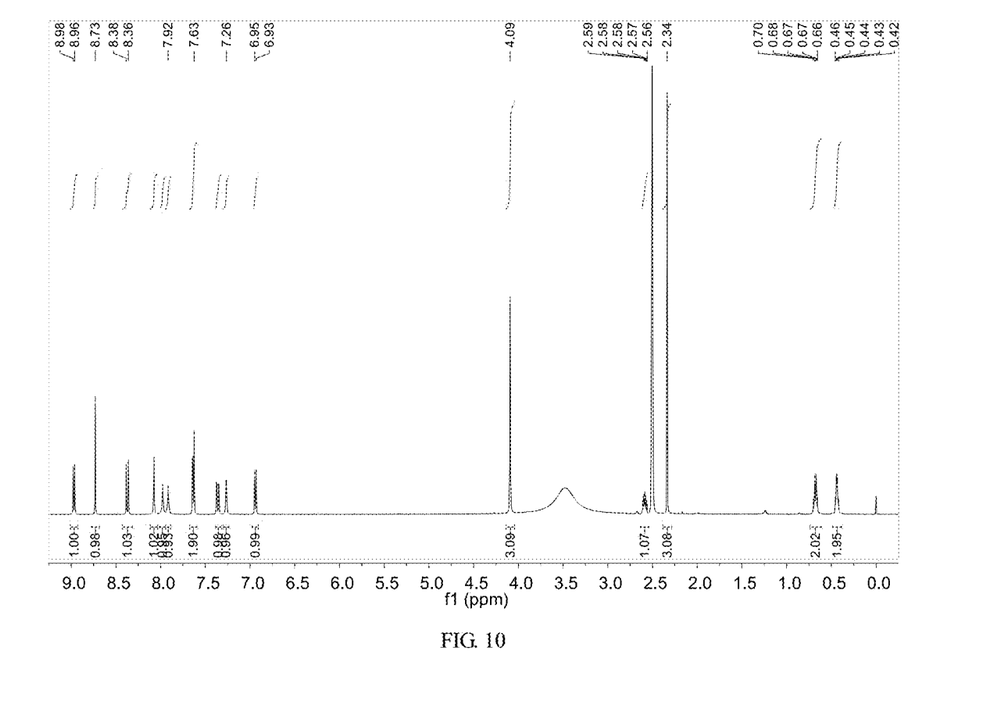
FIG. 10 shows a $^1$HNMR spectrum of crystalline Form M of lenvatinib mesylate

The $^1$H NMR spectrum of Form M is depicted in FIG. 10, which indicates there is no solvent residual. And the $^1$H NMR data are: $^1$H NMR (400 MHz, DMSO-d6) δ 8.97 (d, J=6.5 Hz, 1H), 8.73 (s, 1H), 8.37 (d, J=9.1 Hz, 1H), 8.07 (s, 1H), 7.98 (s, 1H), 7.92 (s, 1H), 7.68-7.59 (m, 2H), 7.36 (dd, J=9.1, 2.8 Hz, 1H), 7.27 (d, J=2.8 Hz, 1H), 6.94 (d, J=6.5 Hz, 1H), 4.09 (s, 3H), 2.58 (ddd, J=10.5, 6.9, 3.4 Hz, 1H), 2.34 (s, 3H), 0.74-0.61 (m, 2H), 0.49-0.39 (m, 2H).

Figure 11:
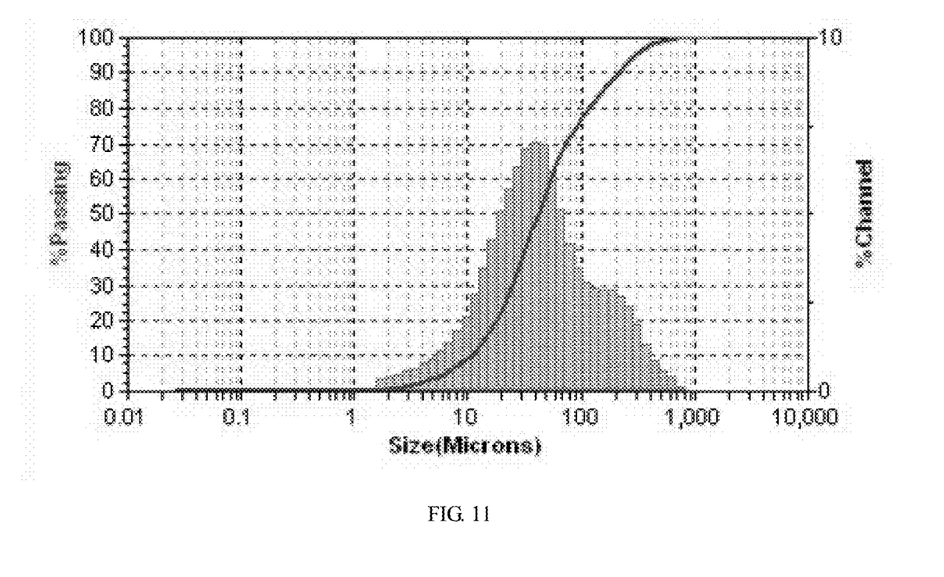
FIG. 11 shows a PSD diagram of crystalline Form M of lenvatinib mesylate

The particle size distribution diagram of Form M is shown in FIG. 11 and the data are list in Table 5. The result shows that the particle size distribution of Form M is normal, and the average particle size (MV) is about 80.5 μm.

TABLE 5

| the particle size distribution of Form M | | | | | |
|---|---|---|---|---|---|
| Form | MV (μm) | SD (μm) | D10 (μm) | D50 (μm) | D90 (μm) |
| Form M | 80.5 | 66.3 | 10.6 | 41.9 | 212.4 |

Mv: Average particle size calculated by volume.
SD: Standard deviation
D10: particle size which accounts for 10% of the particle size distribution (volume distribution).
D50: particle size which accounts for 50% of the particle size distribution (volume distribution), also known as the median diameter.
D90: particle size which accounts for 90% of the particle size distribution (volume distribution).

Example 6

10.11 g of Form B of Lenvatinib was added into 300 mL of acetonitrile at −5° C. in 10 minutes, with a speed of 200 r/min. Then acetonitrile solution of methanesulfonic acid (the volumes of methanesulfonic acid and acetonitrile are 1.6 mL and 25 mL) was added in over 4 hours. The mixture was aged for 5 hours at −5° C. with a stirring speed of 150 r/min. Then the suspension was vacuum filtered at 5° C. under nitrogen protection for 10 minutes, and the obtained wet cake was vacuum dried to obtain a dry solid. The dry solid was purged under humid nitrogen (20% RH-30% RH) atmosphere for 24 hours to obtain the final product.

Figure 12:
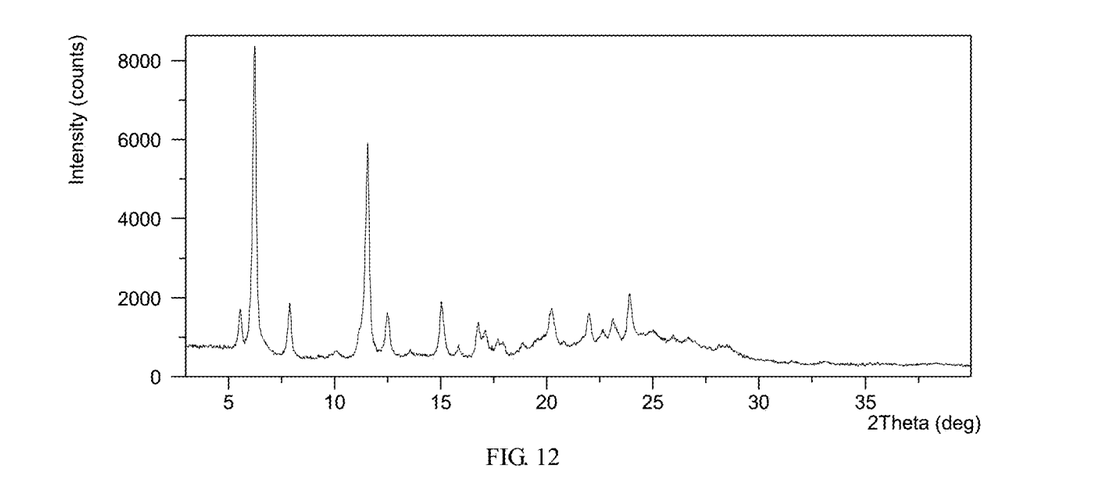
FIG. 12 shows an XRPD pattern of crystalline Form M of lenvatinib mesylate

The obtained final product is Form M, and the XRPD pattern is displayed in FIG. 12. The XRPD data are shown in Table 6.

TABLE 6

| 2θ | d spacing | Intensity % |
|---|---|---|
| 5.60 | 15.76 | 8.06 |
| 6.28 | 14.06 | 100.00 |
| 7.95 | 11.11 | 18.86 |
| 11.60 | 7.63 | 64.03 |
| 12.59 | 7.03 | 17.84 |
| 15.02 | 5.90 | 14.55 |
| 15.86 | 5.58 | 3.63 |
| 16.75 | 5.29 | 10.02 |
| 17.18 | 5.16 | 7.98 |
| 17.95 | 4.94 | 5.63 |
| 18.91 | 4.69 | 5.99 |
| 20.19 | 4.40 | 13.64 |
| 22.01 | 4.04 | 13.70 |
| 23.18 | 3.84 | 13.43 |
| 23.91 | 3.72 | 18.78 |
| 26.74 | 3.33 | 7.48 |
| 28.78 | 3.10 | 3.82 |

Example 7

10.14 g of Form B of Lenvatinib was added into 300 mL of acetonitrile at −5° C. for 10 minutes, with a speed of 200 r/min. Then acetonitrile solution of methanesulfonic acid (the volumes of methanesulfonic acid and acetonitrile are 1.6 mL and 25 mL) was added in over 4 hours. The mixture was aged for 5 hours at −5° C. with a stirring speed of 150 r/min. Then the suspension was vacuum filtered under nitrogen protection for 10 minutes, and the obtained wet cake was vacuum dried to obtain a dry solid. The dry solid was purged under humid nitrogen (20% RH-30% RH) atmosphere for 24 hours to obtain the final product.

Figure 13:
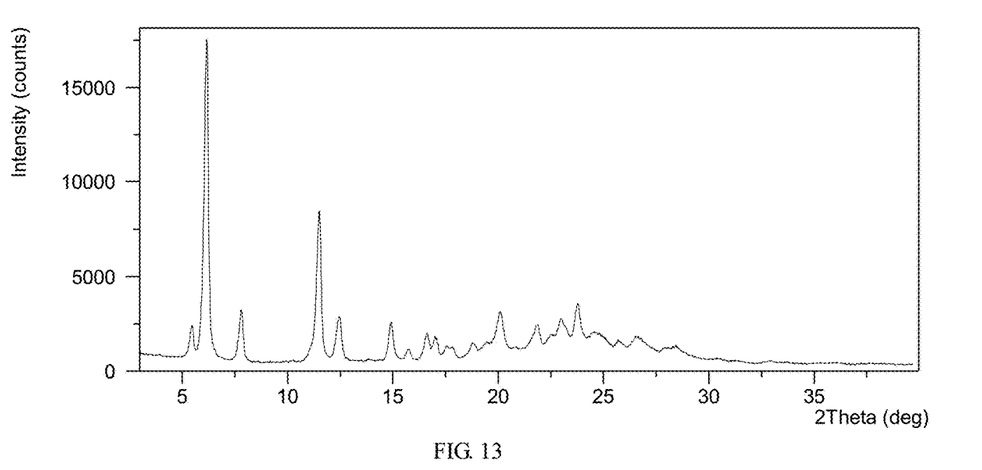
FIG. 13 shows an XRPD pattern of crystalline Form M of lenvatinib mesylate

The obtained final product is Form M, and the XRPD pattern is displayed in FIG. 13. The XRPD data are shown in Table 7.

TABLE 7

| 2θ | d spacing | Intensity % |
|---|---|---|
| 5.47 | 16.15 | 10.55 |
| 6.18 | 14.30 | 100.00 |
| 7.81 | 11.32 | 16.32 |
| 11.51 | 7.69 | 46.49 |
| 12.48 | 7.09 | 13.67 |
| 14.92 | 5.94 | 12.66 |
| 15.69 | 5.65 | 3.99 |
| 16.60 | 5.34 | 8.95 |
| 16.98 | 5.22 | 7.68 |
| 17.56 | 5.05 | 5.07 |
| 17.85 | 4.97 | 4.58 |
| 18.75 | 4.73 | 5.91 |
| 19.44 | 4.57 | 6.50 |
| 20.15 | 4.41 | 15.01 |
| 21.88 | 4.06 | 11.48 |
| 22.48 | 3.95 | 9.02 |
| 22.98 | 3.87 | 14.06 |
| 23.78 | 3.74 | 18.82 |
| 24.48 | 3.64 | 9.67 |
| 25.00 | 3.56 | 8.43 |
| 25.70 | 3.47 | 7.32 |
| 26.56 | 3.36 | 8.36 |
| 27.93 | 3.19 | 4.97 |
| 28.45 | 3.14 | 5.52 |

Example 8

Figure 14:
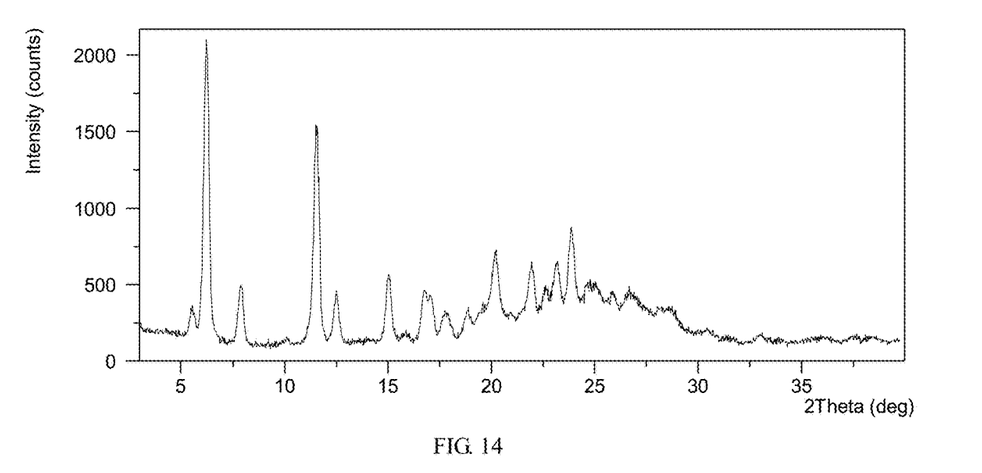
FIG. 14 shows an XRPD pattern of crystalline Form M of lenvatinib mesylate

20.01 g Form B of Lenvatinib was added into 600 mL of acetonitrile at −5° C. in 20 minutes, with a stirring rate of 200 r/min. Then acetonitrile solution of methanesulfonic acid (the volumes of methanesulfonic acid and acetonitrile are 3.2 mL and 50 mL) was added in over 4 hours. The mixture was aged for 5 hours at −5° C. with a stirring speed of 200 r/min. Then the suspension was vacuum filtered under nitrogen protection for 20 minutes, and the obtained wet cake was vacuum dried. The obtained solid is Form M, and the XRPD pattern is displayed in FIG. 14. The XRPD data are shown in Table 8.

TABLE 8

| 2θ | d spacing | Intensity % |
|---|---|---|
| 5.51 | 16.04 | 11.71 |
| 6.30 | 14.04 | 100.00 |
| 7.95 | 11.13 | 21.71 |
| 10.07 | 8.78 | 2.15 |
| 11.56 | 7.66 | 88.16 |
| 12.49 | 7.09 | 21.10 |
| 15.09 | 5.87 | 26.45 |
| 15.83 | 5.60 | 4.42 |
| 16.72 | 5.30 | 20.79 |
| 17.07 | 5.19 | 19.20 |
| 17.62 | 5.03 | 10.38 |
| 18.83 | 4.71 | 13.63 |
| 20.20 | 4.40 | 36.94 |
| 21.92 | 4.05 | 31.63 |
| 22.53 | 3.95 | 20.93 |
| 23.18 | 3.84 | 33.36 |
| 23.82 | 3.74 | 46.27 |
| 24.63 | 3.62 | 23.20 |
| 25.11 | 3.55 | 22.09 |
| 25.83 | 3.45 | 20.62 |
| 26.60 | 3.35 | 19.90 |
| 28.72 | 3.11 | 13.09 |
| 30.41 | 2.94 | 5.36 |
| 32.97 | 2.72 | 2.99 |

What is claimed is:

1. A crystalline Form M of compound (I) mesylate, wherein the X-ray powder diffraction pattern shows at least three characteristic peaks at 2theta values of 11.4°±0.2°, 6.2°±0.2°, 15.1°±0.2°, 12.5°±0.2°, 23.8°±0.2°, 21.9°±0.2°, 7.9°±0.2° and 20.2±0.2° using CuKα radiation (I)

2. The crystalline Form M of compound (I) mesylate according to claim 1, wherein the X-ray powder diffraction pattern shows characteristic peaks at 2theta values of 6.2°±0.2°, 11.4°±0.2° and 15.1°±0.2°.

3. The crystalline Form M of compound (I) mesylate according to claim 2, wherein the X-ray powder diffraction pattern shows one or two or three characteristic peaks at 2theta values of 7.9°±0.2°, 12.5°±0.2° or 21.9°±0.2°.

4. The crystalline Form M of compound (I) mesylate according to claim 2, wherein the X-ray powder diffraction pattern shows one or two characteristic peaks at 2theta values of 23.8°±0.2° and 20.2°±0.2°.

5. The crystalline Form M of compound (I) mesylate according to claim 1, wherein an X-ray powder diffraction pattern is substantially as shown in FIG. 8.

6. The crystalline Form M of compound (I) mesylate according to claim 1, wherein the Fourier Transform Infrared (FT-IR) spectroscopy has the following absorption bands expressed in reciprocal wave numbers: 535.72±1 cm$^{-1}$ and 1400.53±1 cm$^{-1}$.

7. The crystalline Form M of compound (I) mesylate according to claim 6, wherein Fourier Transform Infrared (FT-IR) spectrometer has the following absorption bands expressed in reciprocal wave numbers: 1190.77±1 cm$^{-1}$ and 1692.73±1 cm$^{-1}$.

* * * * *